(12) United States Patent
Dutcher et al.

(10) Patent No.: US 6,589,744 B2
(45) Date of Patent: Jul. 8, 2003

(54) METHOD AND KIT FOR IDENTIFICATION FOR NUCLEIC ACID MODIFICATION ENZYMES AND INHIBITORS THEREOF

(75) Inventors: Robert Calvin Dutcher, Raleigh, NC (US); Michael William Bauer, Holly Springs, NC (US); Paul Bernasconi, Chapel Hill, NC (US)

(73) Assignee: Syngenta Participations AG, Basel (CH)

(*) Notice: Subject to any disclaimer, the term of this patent is extended or adjusted under 35 U.S.C. 154(b) by 0 days.

(21) Appl. No.: 09/994,346

(22) Filed: Nov. 26, 2001

(65) Prior Publication Data

US 2003/0099953 A1 May 29, 2003

(51) Int. Cl.[7] .......................... C12Q 1/68; C12P 19/34; C07H 21/02; C07H 21/04
(52) U.S. Cl. .................. 435/6; 435/91.1; 435/91.2; 536/23.1; 536/24.3
(58) Field of Search .......................... 435/6, 91.1, 91.2; 536/23.1, 24.3

(56) References Cited

U.S. PATENT DOCUMENTS

| | | | | |
|---|---|---|---|---|
| 5,593,867 A | | 1/1997 | Walker et al. ............. | 435/91.2 |
| 5,686,243 A | | 11/1997 | Royer et al. ............... | 435/6 |
| 5,705,344 A | * | 1/1998 | Giordano et al. .......... | 435/6 |
| 5,786,139 A | | 7/1998 | Burke et al. ............... | 435/6 |
| 6,100,039 A | | 8/2000 | Burke et al. ............... | 435/6 |
| 6,153,384 A | * | 11/2000 | Lynch et al. ............... | 435/6 |

FOREIGN PATENT DOCUMENTS

| | | | | |
|---|---|---|---|---|
| EP | 0 320 308 A2 | 6/1989 | ............ | C12Q/1/68 |
| EP | 0 382 433 A2 | 8/1990 | ............ | C12Q/1/68 |
| WO | WO 92/18650 | 10/1992 | ............ | C12Q/1/68 |

OTHER PUBLICATIONS

Spears, P. A. et al., "Simultaneous Strand Displacement Amplification and Fluorescence Polarization Detection of Chlamydia trachomatis DNA", Anal. Biochem., vol. 247, pp. 130–137 (1997).*

Earnshaw, D.L. et al., *Time–Resolved Fluorescence Energy Transfer DNA Helicase Assays for High Throughput Screening Journal of Biomolecular Screening*, vol. 4, No. 5 (1999) pp. 239–248.

Kwong, A.D. and Risano, C. "Development of a hepatitis C Virus RNA Helicase High Throughput Assay" in: eds. Kinchington, D. and Schinazi R.F., *Antiviral Methods and Protocols*, (New Jersey, Humana Press, 2000) pp. 98–116.

Li, Z., et al, *An Ultra–High Throughput Screening Approach for an Adenine Transferase Using Fluorescence Polarization Journal of Biomolecular Screening*, vol. 5, No. 1 (2000) pp. 31–37.

Montecucco, A. et al., *DNA unwinding and inhibition of T4 DNA ligase by anthracyclines Nucleic Acids Research*, vol. 16, No. 9 (1988) pp. 3907–3918.

Tong, J., *Ligation reaction specificities of an NAD+–dependent DNA ligase from the hyperthermophile Aquifex aeolicus Nucleic Acids Research*, vol. 28, No. 6 (2000), pp. 1447–1454.

Chen et al, *A Homogeneous, Ligase–Mediated DNA Diagnostic Test Genome Research*, vol. 8. No. 5 (May 1, 1998) pp. 549–556.

Hicham et al., *A novel high throughput screening assay for HCV NS3 helicase activity Antiviral Research*, vol. 26 (2000), pp. 181–193.

Houston, P. and Thomas, K., *Spectrophotometric assay for enzyme–mediated unwinding of double–stranded DNA Proceedings of the National Academy of Science (US)*, vol. 91, (Jun. 1994) pp. 5471–5474.

Kwok, P.Y., *High–throughput genotyping assay approaches Pharmacogenomics*, vol. 1(1), (2000), pp. 95–100.

Murakami et al., *Fluorescent–labeled oligonucleotide probes: detection of hybrid formation in solution by fluorescence polarization spectroscopy Nucleic Acids Research*, vol. 19, No. 15 (1991) pp. 4097–4102.

Nasir, M. S. and Jolley, M. E., *Fluorescence Polarization: An Analytical Tool for Immunoassay and Drug Discovery Combinatorial Chemistry & High Throughput Screening*, vol. 2 (1999), pp. 177–190.

* cited by examiner

Primary Examiner—Kenneth R. Horlick
Assistant Examiner—Teresa Strzelecka
(74) Attorney, Agent, or Firm—Bruce Vrana

(57) ABSTRACT

A method and kit for detecting nucleic acid modification enzyme activity by monitoring the change in fluorescence polarization upon the change in mass of a fluorescently labeled oligo. A nucleic acid substrate comprises a template having a nucleic acid sequence annealed to a labeled oligo, wherein there is a nick or break located between the adjacent ends of the template and the labeled oligo. A nucleic acid modification enzyme is added to the substrate to form a reaction mixture. A stop reagent may or may not be used to further process the reaction mixture. A test compound is added to the reaction mixture, preferably prior to addition of the nucleic acid modification enzyme, whereby the resulting fluorescence polarization signal is compared to a standard signal to determine if the test compound inhibits nucleic acid modification enzyme activity.

14 Claims, 3 Drawing Sheets

FIG. 1 a) Without Inhibitor

```
RCD04              5'- TTTTGCCTCGCTGCCGTCGCCATTTTACGTCGTGACTTCTCACTCCAGTCCTAGTCTAGA-3'

RCD10(P) +         3'- TTTTCGGAGCGACGGCAGCGGTAAAATGCAGCAC-FL -5'
RCD11(F)
                                              PO4
                                      ATP
                                         ) DNA Ligase
                                  ADP + Pi RCD04              5'- TTTTGCCTCGCTGCCGTCGCCATTTTACGTCGTGACTTCTCACTCCAGTCCTAGTCTAGA-3'

RCD12(F)           3'- TTTTCGGAGCGACGGCAGCGGTAAAATGCAGCAC-FL -5'

1M NaOH

RCD04              5'- TTTTGCCTCGCTGCCGTCGCCATTTTACGTCGTGACTTCTCACTCCAGTCCTAGTCTAGA-3'

RCD12(F)           3'- TTTTCGGAGCGACGGCAGCGGTAAAATGCAGCAC-FL -5'        HIGH mP
``` b) With Inhibitor

```
RCD04              5'- TTTTGCCTCGCTGCCGTCGCCATTTTACGTCGTGACTTCTCACTCCAGTCCTAGTCTAGA-3'

RCD10(P) +         3'- TTTTCGGAGCGACGGCAGCGGTAAAATGCAGCAC-FL -5'
RCD11(F)
                                              PO4
                                      ATP
                                         )X DNA Ligase
                                  ADP + Pi RCD04              5'- TTTTGCCTCGCTGCCGTCGCCATTTTACGTCGTGACTTCTCACTCCAGTCCTAGTCTAGA-3'

RCD10(P) +         3'- TTTTCGGAGCGACGGCAGCGGTAAAATGCAGCAC-FL -5'
RCD11(F)
                                              PO4

1M NaOH

RCD04              5'- TTTTGCCTCGCTGCCGTCGCCATTTTACGTCGTGACTTCTCACTCCAGTCCTAGTCTAGA-3'

RCD10(P)           3'- TTTTCGGAGCGACGGCAGCGGTAAAAT-PO4 5'    3'GCAGCAC-FL -5'    LOW mP
RCD11(F)
```

FIG. 3 a) Without Inhibitor

RCD(X)  AATAGCCTCGCTGCCGTCGCCATTTTACGTCGTGACTTCTCACTCCAGTCCTAGTCTAGA-3'
        A ||||||||||||||||||||||||||||||||||||||||||||||||||||||||
RCDY(F) + AAATCGGAGCGACGGCAGCGGTAAAATGCAGCACTGAAGAGTGAGGTCAGGATCAGA-FL -5'

ATP
                       ) Nucleic Acid Helicase
                ADP + Pi

RCD(X)  AATAGCCTCGCTGCCGTCGCCATTTTACGTCGTGACTTCTCACTCCAGTCCTAGTCTAGA-3'
        A
RCDY(F) + A
        A
        ATCGGAGCGACGGCAGCGGTAAAATGCAGCACTGAAGAGTGAGGTCAG

GATCAGA-FL -5'
                                                         Low mP b) With Inhibitor

RCD(X)  AATAGCCTCGCTGCCGTCGCCATTTTACGTCGTGACTTCTCACTCCAGTCCTAGTCTAGA-3'
        A ||||||||||||||||||||||||||||||||||||||||||||||||||||||||
RCDY(F) + AAATCGGAGCGACGGCAGCGGTAAAATGCAGCACTGAAGAGTGAGGTCAGGATCAGA-FL -5'

ATP
                       )X DNA Ligase
                ADP + Pi

RCD(X)  AATAGCCTCGCTGCCGTCGCCATTTTACGTCGTGACTTCTCACTCCAGTCCTAGTCTAGA-3'
        A ||||||||||||||||||||||||||||||||||||||||||||||||||||||||
RCDY(F) + AAATCGGAGCGACGGCAGCGGTAAAATGCAGCACTGAAGAGTGAGGTCAGGATCAGA-FL -5'

High mP

METHOD AND KIT FOR IDENTIFICATION FOR NUCLEIC ACID MODIFICATION ENZYMES AND INHIBITORS THEREOF

FIELD OF THE INVENTION

The present invention relates to a method for identifying enzymes and inhibitors of enzymes involved in nucleic acid modification, and particularly a homogenous assay for identifying nucleic acid ligases and helicases and inhibitors thereof using fluorescence polarization to detect the change in mass of a fluorescently labeled oligo.

BACKGROUND OF THE INVENTION

Nucleic acid modification enzymes, particularly DNA ligases and helicases, play a critical role in nucleic acid replication, excision repair, and genetic recombination. Ligases catalyze the ligation of nucleic acid strand breaks generated during various cellular metabolic events such as nucleic acid replication and recombination, and in response to strand breaks produced by various environmental factors. DNA helicases unwind DNA as part of the replication process, and to facilitate removal and substitution of single strand nucleotides. The reaction mechanism of nucleic acid ligases and helicases has mainly been studied using radioisotope-labeled substrates and gel electrophoresis. Such techniques are time consuming, require disposal of environmentally dangerous substances, and limit the number of samples that can be assayed. Therefore, there is a need for an assay that is quick and does not require use of radiolabels or gel electrophoresis.

Fluorescence polarization has also been used to analyze fluorescently labeled molecules and ligands. Representative samples of such methods are disclosed in U.S. Pat. No. 5,789,249, which discloses the detection of nucleic acid cleavage enzymes, such as restriction enzymes; U.S. Pat. No. 4,902,630, which discloses use of fluorescence polarization to measure the amount of tracer-antibody complex produced in a competitive binding immunoassay; U.S. Pat. No. 4,681,859, which describes an immunoassay for detecting the presence of a ligand in an aqueous sample based upon its competition with a fluorescently labeled ligand for the binding site on an anti-ligand partner; and U.S. Pat. No. 4,751,190, which discloses another fluorescence polarization method for use in immunoassays. However, the present art does not disclose detecting enzymes used in the processes of nucleic acid repair and replication using fluorescence polarization according to the method and kit of the present invention.

SUMMARY

The method and kit of the present invention uses fluorescence polarization to identify, in a homogeneous format, inhibitors of nucleic acid modification enzyme activity, in particular, nucleic acid ligase and helicase activity. Nucleic acid ligase repairs single-strand breaks, whereas helicases are often referred to as relaxing enzymes, because they unwind double stranded nucleic acids prior to replication and nucleic acid repair. The method and kit of the present invention measure DNA ligase and helicase activity, as well as the effect of inhibitors on such activities, using fluorescence polarization.

In one embodiment of the present invention, nucleic acid ligases and their inhibitors are identified by providing a first oligo, a second oligo, and a third fluorescein-labeled oligo, wherein the second and third oligos are complementary to adjacent sections of the first oligo and are capable of annealing thereto. The oligos are annealed to form a double stranded enzyme substrate with a break or nick between the second and third oligos. The substrate of the present invention is then diluted to the appropriate concentration in a buffer that is compatible with nucleic acid ligase activity. A nucleic acid ligase, an inhibitor or test compound, and the substrate are added together to form a reaction mixture, which is incubated for a time sufficient for reactions to occur. A stop reagent, such as NaOH, is added to dissociate the oligos and fluorescence polarization detects whether the test compound repaired the break between the second and third oligos to form a longer fourth oligo. Increased fluorescence polarization relative to that of the fluorescein-labeled third oligo indicates a ligation product (fourth oligo) is formed and that the test compound did not inhibit the activity of the ligase. A fluorescence polarization corresponding to the fluorescence polarization signal of the third oligo indicates that the test compound inhibits enzyme activity.

In another embodiment of the present invention a substrate comprised of two oligos is used to identify inhibitors of nucleic acid ligases and helicases. One oligo includes a section that is complementary and anneals to the second oligo, which is fluorescently labeled. A break or nick is located between the adjacent ends of the two oligos. The entire structure or substrate forms a double stranded hairpin nucleic acid molecule, which is characterized by a particular fluorescence polarization signal. In the presence of a helicase, unwinding and separation of the small fluorescein-labeled second oligo from the larger unlabelled oligo occurs. In the presence of ligase, the break between the two oligo is repaired, thereby linking the two oligos together to form a longer fluorescent-labeled oligo. Relevant inhibitors, would of course, prevent or inhibit the formation of these enzymatic products. Due to the different degrees of polarization of emitted light from reaction mixtures, the invention detects the presence of the enzymes and relevant inhibitors.

The invention also includes a kit for analyzing the activity of nucleic acid ligases and helicases and inhibitors thereof. The kit contains substrates and enzymes, along with an assay support structure for carrying out the steps of the method.

The method of using fluorescence polarization to assay the activity of nucleic acid ligases and helicases is limited to neither the use of fluorescein as the fluorescent label, the use of the specific oligos or numbers thereof, the biotin/avidin used as ligands for affecting a change in mass of an oligonucleotide, or the set of annealed oligonucleotides used.

The methods and kits of the present invention can for example be used to screen for crop protection chemicals, such as herbicides, insecticides or fungicides, antibiotics, anti-viral agents, anti-tumor agents, or compounds, which modulate and/or regulate the function of clinically important proteins.

An advantage of the methods and kits of the present invention is that they are particularly well-suited for high-throughput assays.

BRIEF DESCRIPTION OF THE DRAWINGS

FIG. 1(a) shows a break between the second and third oligos that is repaired by a nucleic acid ligase to form an oligo characterized by a high fluorescence polarization signal.

FIG. 1(b) shows inhibition of a nucleic acid ligase by an inhibitor added to the reaction mixture that results in an oligo having a low mP.

FIG. 3(a) shows addition of a helicase to a substrate, wherein the unwinding of the nucleic acid substrate causes a small 5' fluorescently-labeled oligo to unwind and separate from the template.

FIG. 3(b) shows the effect of an inhibitor on helicase activity.

DETAILED DESCRIPTION OF THE INVENTION

Figure 2:
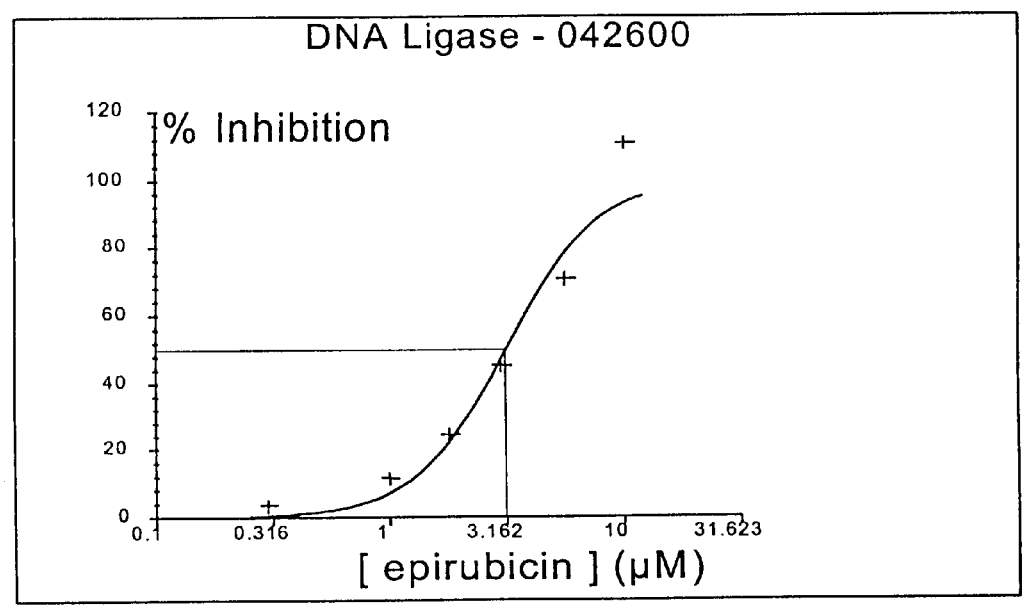
FIG. 2 shows that 100% ligase inhibition is obtained with Epirubicin at 10 µM.

Fluorescence polarization allows for development of homogenous screening assays, whereby it is not necessary to separate the products from the reaction between the biological compound and the fluorescent substance and the unreacted fluorescent substance. The method of the present invention is a high throughput assay that uses fluorescence polarization to identify inhibitors of nucleic acid ligases and helicases in a panel or library of test compounds, and is based on the comparison of the fluorescence polarization signals.

The term "ligase" refers to any enzyme that catalyzes the linkage of two nucleic acids or nucleotides.

The term "helicase" refers to any enzyme that separates nucleic acid strands.

"Fluorescent substance" refers to a compound having fluorescence emitting properties such that the requisite activity for fluorescence polarization is maintained. In the preferred embodiment of the invention, fluorescein is used as the active label. Suitable fluorescein labels for use in the invention include, for example, fluorescein-maleimide, fluorescein-iodoacetamide, 5-bromomethyl-fluorescein, fluorescein-succinimidyl ester, fluorescein-C6-succinimidyl ester, carboxy-fluorescence fluorescein isothiocynates, triazinylaminofluoresceins, and may other labels well known in the art. Other fluorescent labels may also be used in the present invention, including but not limited to lucifer yellow, texas red, and rhodamine.

The term "nucleic acid" refers to multiple nucleotides attached to form a single or double stranded polynucleotide, which can be natural or synthetically derived, and includes modifications of nucleic acids.

The terms "break" or "nick" are used interchangeably herein, and refer to the lack of a covalent bond between two adjacent nucleotides of a nucleic acid strand.

Fluorescence polarization techniques are well known to those skilled in the art. For a detailed explanation of fluorescence polarization, refer to Li et al., Journal of Biomolecular Screening, V5 (1)31–37 and Pope et al., Drug Discovery Today, V4 (8) 350–362, August 1999.

The method and kit of the present invention use substrates for detection of nucleic acid modification enzyme activity. In summary, the present invention provides a nucleic acid substrate comprised of a template and a labeled oligo complimentary and annealed to a portion of the template. A nucleic acid modification enzyme is added to the oligo substrate to form a reaction mixture. A stop reagent may or may not be used to further process the reaction mixture. The fluorescence polarization of the reaction mixture is compared to at least one standard fluorescence polarization signal. A test compound may be added to the reaction mixture, whereby the resulting fluorescence polarization signal is compared to a standard signal to determine if the test compound inhibits nucleic acid modification enzyme activity.

EXAMPLE I

Detection of Ligase Activity

One embodiment of the invention provides a first oligo having adjacent sections that are complementary to second and labeled third oligos. The second and third oligos anneal to their complementary sections of the first oligo to form a substrate having a break between the second and third oligos. The "template" referred to herein corresponds to or includes a section of nucleic acid that is complementary to the labeled third oligo. In this Example I, the "template" corresponds to the nucleic acid sequence of the first and second oligos, wherein a section of the nucleic acid sequence is complementary and anneals to the third labeled oligo. The "template" annealed to the labeled oligo forms what is referred to herein as the "substrate."

A ligase is added to the substrate in an appropriate buffer to form a reaction mixture. A stop reagent is later added to unanneal the oligos. Nucleic acid repair is detected by comparing the fluorescence polarization of the reaction mixture with a fluorescence polarization standard. FIG. 1(a) shows the break between the second and third oligos that is repaired by a nucleic acid ligase to form an oligo characterized by a high fluorescence polarization signal. FIG. 1b illustrates inhibition of nucleic acid ligase by an inhibitor added to the reaction mixture that results in an oligo having a low mP as described in more detail below.

Referring to FIGS. 1a and 1b, and by way of example only, a first oligo RCD04 (5'TTT TGC CTC GCT GCC GTC GCC ATT TTA CGT CGT GAC TTC TCA CTC CAG TCC TAG TCT AGA, SEQ ID NO:1), a second oligo RCD10P (5'PO4-TAA AAT GGC GAC GGC AGC GAG GCT TTT, SEQ NO:2), and a third fluorescein labeled oligo RCD11F (5'-Fluorescein-CACGACG) are synthesized using known methods and stored prior to use at −20° C. at 100 µM in 10 mM Tris-HCl, pH 8.

The method of the present invention uses *Arabidopsis thaliana* nucleic acid ligase, Accession No. X97924 (DNAL, EC 6.5.1.1.). This nucleic acid ligase is an ATP-dependent enzyme that catalyzes the joining of complementary 5' and 3' overhangs as well as the repair of single strand breaks, and is a homolog of ATP-dependent DNA ligase I such as T4 nucleic acid ligase (Taylor et al. (1998) Plant J. 14:75–81). However, the method of the present invention can utilize other nucleic acid ligases, including those that are not ATP-dependent. For the method of the present invention, the nucleic acid ligase is stored in a buffer comprising 10 mM Tris-HCl, pH 7.5; 50 mM KCl; 1 mM DTT; 0.1 mM EDTA; 200 µg/mL BSA; and 50% glycerol. The nucleic acid ligase typically has very high specific activity. Thus, the enzyme dilution showing maximum sensitivity is determined empirically before screening.

The oligos RCD10P and RCD11F are annealed (Tong et al., Nucleic Acids Research 28, 1447–1454, 2000) to RCD04 in an oligo annealing mixture of 17 µL of 100 µM RCD04, 17 µL of 100 µM RCD10P, 17 µL 100 µM RCD11F, 17 µL of 10×substrate annealing buffer comprising 500 mM NaCl, 100 mM Tris-HCl, pH 7.9, 100 mM MgCl2, 10 mM and DTT, and H₂O to a volume of 170 ul. The 170 ul of oligo annealing mixture is incubated for 5 minutes at 95C. then cooled at room temperature for 60 minutes in the dark. After annealing, the oligos are diluted in a 10× Substrate Assay Buffer comprising 500 mM Tris-HCl, pH 7.5; 100 mM MgCl2; 100 mM DTT; 10 mM ATP; and 250 ug/mL BSA. The mixture is aliquoted into each well of a 384 well plate. FIGS. 1a and 1b depict the substrate comprised of the oligos RCD10P and RCD11F annealed to the oligo RCD04.

Reagents are generally prepared for a 384 well plate at 110% of the level required. 338 ul of an enzyme stock solution is mixed with a set volume of an enzyme dilution buffer to form an appropriately diluted enzyme mixture. A substrate screening stock is formed by adding 170 µL of the oligo annealing mixture, which has been incubated as described above, with 338 µL 10× substrate assay buffer and 2873 µL water.

The steps of the method of the invention are as follows:

1) Anneal the oligo substrates by forming the oligo annealing mixture as discussed above.
2) Add 4 µL of an inhibitor or library compound (in 10% DMSO) to each well.
3) Add 8 µL of the Substrate Screening Stock to each well (final concentration=500 nM Oligo)
4) Add 8 µL enzyme mixture to each well to initiate reaction.
5) Incubate, preferably in the dark, for 1 hour at room temperature.
6) Add 10 µL of stop reagent, 1M NaOH, to each well (Hsiao, K., (1991) Nucleic Acids Research, 19, 2787). The stop reagent is added to unanneal the oligos and to dissociate the enzyme from the nucleic acid.
7) Measure fluorescence polarization less than 30 minutes, preferably less than 5 minutes, after the addition of the stop reagent. Tecan (Research Triangle Park, N.C.) Polarion™ is used with the following excitation and emission filters: $\lambda_{ex}$=485 nm and $\lambda_{em}$=535 nm (bandwidth of 24 nm, gain at 90, and 50 flashes/well). Under these conditions 500 nM fluorescein labeled oligo with a signal:noise ratio greater than 20 is detected.

Florescence polarization detects the enzyme-catalyzed formation, in this Example, of an 11.6 kDa fluorescein-labeled fourth oligo (RCD12F, 5'-Fluorescein CAC GAC GTA AAA TGG CGA CGG CAG CGA GGC TTT T, SEQ ID NO:3) resulting from the ligation of the second oligo 5' phosphorylated 8.9 kDa oligo (RCD10P) and the third oligo 5' fluorescein-labeled 2.7 kDa oligo (RCD11F). The ligation product, RCD12F, is detected by its increased fluorescence polarization relative to the starting materials or by comparing it to a standard.

Referring to FIG. 1(b) and by way of example only, addition of a nucleic acid ligase inhibitor, such as epirubicin (Montecucco et al. (1988) Nuc. Acids Res. 16, 3907–3918), prevents repair and formation of RCD12F, and the fluorescence polarization signal is that of the smaller fluorescein labeled RCD11F, which is significantly less than the fluorescence polarization signal of RCD12F. The effect of epirubicin on the activity of the Arabidopsis DNA ligase was investigated using the fluorescence polarization technique. FIG. 2 shows that 100% ligase inhibition is obtained with Epirubicin at 10 µM. The results shown in FIG. 2 indicate an IC50 of 3 µM for the Arabidopsis enzyme. This is nearly identical to the IC50 of 2.7 µM previously determined for the T4 DNA ligase using radiolabeled substrates and PAGE gel shift assays. (Montecucco et al.)

Standards are developed by synthesizing a positive control. This standard or positive control corresponds in the above example to the formation of RCD12F due to ligase activity, i.e., use of active nucleic acid ligase with no inhibitor present. The resulting fluorescence polarization signal of the synthetic positive control corresponds to 0% inhibition. A negative control is generated by using heat-killed DNA ligase with no measurable activity. Since no ligation occurs, the labeled product (negative control) is a smaller oligo identified in FIG. 1 as RCD11F. The resulting fluorescence polarization signal is equivalent to 100% inhibition. Using controls, an assay quality assessment is performed using the screening window coefficient, also known as the Z-factor (Zhang et al. (1999) J. Biomolecular Screening 4, 67–73). A value of >0.5 is determined to be equivalent to "an excellent assay".

EXAMPLE II

Analysis of Helicase Activity

Referring to FIGS. 3a and 3b, nucleic acid helicase enzymes and inhibitors thereof can also be tested according to the method of the present invention by using a fluorescently-labeled oligonucleotide and measuring its hybridization with a complementary oligonucleotide. For example, an enzyme substrate is formed by mixing a first oligo or template RCDX (5'-GAC TGG AGT GAG AAG TCA CGA CGT AAA ATG GCG ACG GCA GCG AGG CTA AAA AAT AGC CTC GCT GCC GTC GCC ATT TTA CGT CGT GAC TTC TCA CTC CAG TCC TAG TCT AGA-3', SEQ ID NO:4), and a second labeled oligo RCDYF (GATCAGA-FL-5') in an appropriate substrate annealing buffer, and incubating until the fluorescently-labeled oligo RCDYF anneals to the complementary section of the template to form a double stranded hairpin nucleic acid molecule or substrate having a break or nick located between adjacent ends of the template and the labeled oligo, as shown in FIGS. 3a and 3b. After annealing, the substrate is further diluted in a substrate assay buffer that is compatible with nucleic acid helicase activity. This diluted substrate is added to each well of one or more 384 well plates.

A helicase is diluted in an appropriate amount of enzyme dilution buffer, and added to the substrate to form a reaction mixture and incubated for a sufficient time to react. The helicase catalyzes the unwinding of the double stranded hairpin nucleic acid molecule thereby causing the small 5' fluorescein-labeled oligo RCDYF to unwind and separate from the template RCDX as shown in FIG. 2a. RCDYF is detected by comparing its fluorescence polarization to a standard fluorescence polarization signal. Use of a stop reagent is generally not preferred.

A library of compounds is tested for their ability to inhibit helicase activity by adding each compound to be tested to the reaction mixture, preferably, prior to adding the helicase enzyme. In the presence of an inhibitor, the double stranded nucleic acid molecule will not unwind in the presence of helicase, and the end product is detected by a high mP fluorescence polarization that corresponds to a high mP standard.

To measure helicase activity, a small molecule is synthesized as a positive control. In this Example II, the labeled oligo RCDYF is synthesized. The positive control, therefore, corresponds to the method of the present invention being carried out with a test compound having no enzyme inhibitory activity. A negative control is synthesized by using heat-killed enzyme in the method of the invention. The heat-killed enzyme fails to unwind the hairpin oligo, resulting in a labeled nucleic acid molecule having a fluorescence polarization signal indicating 100% inhibition.

It should be noted that the substrate used to detect ligase activity and inhibition thereof as described in Example I above, can be a double stranded hairpin nucleic acid molecule similar to that described in this Example II. Addition of a stop reagent causes the double stranded hairpin molecule to unanneal. If the enzyme repairs the break, then a relatively high mP fluorescence polarization signal will result. On the contrary, if inhibition of ligase activity occurs, the fluorescence polarization signal will correspond to that of the smaller labeled oligo.

Likewise, the substrate used to detect helicase activity and inhibition thereof as described in this Example II, can be a double stranded DNA substrate as described in Example I. Addition of the helicase will cause the strands to separate, including the smaller labeled strand. An inhibitor of helicase activity would of course, inhibit this activity, resulting in detection of a labeled double stranded DNA substrate in the reaction mixture.

The invention also includes a kit for analyzing the activity of nucleic acid ligases and helicases and inhibitors thereof. The kit contains substrates and enzymes, along with an assay support structure for carrying out the steps of the method.

Discussed immediately below are several non-limiting examples of applications of the method and kit of the present invention.

Genes encoding a DNA ligase and a RNA helicase protein have been isolated from Arabidopsis thaliana and it is hypothesized that homologous proteins are present in other plant species. The ligase and helicase enzymes are essential for the proper development and viability of the individual plant. These enzymes are useful targets to identify new herbicidal compounds that possess herbicidal action, particularly using the methods and kits of the present invention. Taylor, R. M., Hamer, M. J., Rosamond, J., Bray, C. M. (1998) Molecular cloning and functional analysis of Arabidopsis thaliana DNA ligase I homologue. The Plant J. (14): 75–81; Okanami, M., Meshi, T., Iwabuchi, M. (1998) Characterization of a DEAD box ATPase/RNA helicase protein of Arabidopsis thaliana. Nucleic Acids Res. 26: 2638–2643 With the frequency of drug resistant bacterial infections on the rise, previously unexploited targets of antibiotic activity are being investigated. DNA ligases are enzymes that catalyze the joining of breaks in the phosphodiester backbone of DNA molecules. The enzymes play an essential role during DNA replication, repair, and recombination. All DNA ligases follow the same reaction mechanism, but they may use either ATP or $NAD^+$ as a cofactor. ATP-dependent ligases are ubiquitous in eukaryotes, in contrast to $NAD^+$-dependent ligases, which are found exclusively in eubacteria. This difference in cofactor specificity suggests that bacterial DNA ligases may be useful antibiotic targets, and that new antibiotics may be discovered using these targets in the method and kit of the present invention. Kaczmarek, F. S., Zaniewski, R. P., Gootz, T. D., Danley, D. E., Mansour, M. N., Griffor, M., Kamath, A. V., Cronan, M., Mueller, J., Sun, D., Martin, P. K., Benton, B., McDowell, L., Biek, D., Schmid, M. B. (2001) Cloning and Functional Characterization of an $NAD^+$-Dependent DNA Ligase from Staphylococcus aureus. J. Bact. 183: 3016–3024; Lee, J. Y., Chang. C., Song, H, K., Moon, J., Yang, J. K., Kim, H., Kwon, S., Suh, S. W. (2000) Crystal structure of $NAD^+$-dependent DNA ligase: modular architecture and functional implications. EMBO J. 19: 1119–1129; Singleton, M. R., Hakansson, K., Timson, D. J., Wigley, D. B. (1999) Structure of the adenylation domain of an $NAD^+$-dependent DNA ligase. Structure 7: 35–42; Wilkinson, A., Day, J., Bowater, R. (2001) Bacterial DNA ligases. Mol. Micro. 40: 1241–1248

Viral infection and replication commonly involves a separation of duplex nucleic acids. This reaction is catalyzed by helicase, a class of RNA/DNA unwinding enzymes with coupled NTPase activity. Examples of novel viral helicases have been reported in the literature (NS3 associated with the Hepatitis C virus (HCV), and UL5/UL52 associated with the Herpes Simplex virus (HSV)). These, and other, novel viral helicases might be useful targets for effective antiviral therapy. Even in viral systems where host enzymes are used for nucleic acid replication, it may be possible to identify new inhibitory agents, targeted against host helicases, to block infection. Therefore, the methods and kits of the present invention are useful to identify new anti-viral compounds using these targets. Bartenschlager, R. (1997) Candidate Targets for Hepatitis C Virus-Specific Antiviral Therapy. Intervirology 40: 378–393; Hong, Z., Standring, D. N., Baroudy, B., Lau, J. Y-N. (2000) Development of novel anti-HCV therapies: HCV protease, helicase, and polymerase as therapeutic targets. Acta Gastro-Enterologica Belgica. 63: 210–212; Matthews, J. T., Terry, B. J., Field, A. K. (1993) The structure and of the HSV DNA replication proteins: defining novel antiviral targets. Antiviral Res. 20: 89–114; Tai, C., Chi, W., Chen, D., Hwang, L. (1996) The Helicase Activity Associated with Hepatitis C Virus Nonstructural Protein 3 (NS3). J. Virol. 70: 8477–8484

Leukemia is a cancer of the blood-forming organs and is characterized by the replacement of bone marrow with immature white blood cells. The most effective method of treatment involves intensive chemotheraphy. Inhibition of DNA ligase has been determined to be the mode of action for several antileukemic drugs. Continued screening against DNA ligase may result in the discovery of new chemical compounds with increased efficacy toward the DNA ligases of leukemic cells. These compounds might be better able to selectively inhibit replication, and thereby division, of cancer cells.

In similar fashion, the anti-tumor activity of some chemical compounds is also a result of their ability to inhibit DNA ligase. Again, discovery of new chemicals that inhibit DNA ligase activity might be clinically useful as anti-tumor agents. Therefore, the methods and kits of the present invention are useful to identify new anti-tumor compounds using these targets. Montecucco, A., Fontana, M., Focher, F., Lestingi, M., Spadari, S., Ciarrocchi, G. (1991) Specific inhibition of human DNA ligase adenylation by a distamycin derivative possessing antitumor activity. Nucleic Acids Res. 19: 1067–1072; Yang, S-W., Huang, P., Plunkett, W., Becker, F. F., Chan, J. Y. H. (1992) Dual Mode of Inhibition of Purified DNA Ligase I from Human Cells by 9-□-D-Arabinofuranosyl-2-fluoroadenine Triphosphate. J. Biol. Chem. 267: 2345–2349; Ciarrocchi, G., Lestingi, M., Fontana, M., Spadari, S., Montecucco, A. (1991) Correlation between anthracycline structure and human DNA ligase inhibition. Biochem. J. 279: 141–146; David, J. C., Bassez, T., Bonhommet, M., Rusquet, R. (1985) Inhibition of DNA ligase from human thymocytes and normal or leukemic lymphocytes by antileukemic drugs. Cancer Res. 45: 2177–2183; Lamballe, F., Le Prise P. Y., Le Gall, E., David, J. C. (1989) dATP-mediated inhibition of DNA ligase by 2'-deoxycoformycin in T and B cell leukemia. Leukemia 3: 97–103; Lamballe, F., Maniey, D., Boscher, M. Y., Fauchet, R., Le Prise, P. Y., David, J. C. (1988) Effects of clinical combinations of antileukemic drugs on DNA ligase from human thymocytes and normal, stimulated, or leukemic lymphocytes. Leukemia 2: 363–370; Saulier, B., Prigent, C., Boutelier, R., David, J. C. (1988) Peplomycin. DNA breakage and in vivo inhibition of DNA polymerases and ligase from human normal and leukemic cells. Carcinogenesis 9: 965–970

The ability to maintain genomic stability is critical to all organisms. Werner Syndrome and Bloom Syndrome are two examples of human genetic disorders that exhibit genomic instability. The phenotypic characteristics common to both diseases are premature aging and a predisposition to cancer. The clinical phenotype of these disorders is presumed to result from impaired function of specific proteins (WRN associated with Werner Syndrome and BLM associated with Bloom's Syndrome) functioning in a pathway of nucleic acid metabolism. These proteins show strong similarity to helicases, particularly the DEXH box-containing DNA helicases. Chemical compounds that can modulate and/or regulate the function of these impaired proteins may be clinically significant for increasing the quality of life of individuals suffering from these, and other, genetic disorders.

The foregoing is considered as illustrative only of the principles of the invention. Further, since numerous modifications and changes will readily occur to those skilled in the art, it is not desired to limit the invention to the exact construction and operation shown and described herein. Therefore, accordingly, all suitable modifications and equivalents fall within the scope of the invention.

What is claimed is:
1. A method for detecting the activity of nucleic acid modification enzymes comprising:
   a) providing a substrate comprising a nucleic acid template and a labeled oligo, wherein a portion of said template is complimentary to said labeled oligo and is annealed thereto;
   b) providing a break between the adjacent ends of said template and said labeled oligo;
   c) mixing said substrate with a nucleic acid modification enzyme to form a reaction mixture;
   d) incubating said reaction mixture for a time sufficient for said enzyme to act on said substrate;

e) optionally, adding a stop reagent to said reaction mixture;

f) measuring a fluorescence polarization signal of said reaction mixture; and g) comparing said fluorescence polarization signal of said reaction mixture with a standard fluorescence polarization signal.

2. A method for detecting the activity of nucleic acid modification enzymes according to claim 1, further comprising mixing a test compound with said reaction mixture for the purpose of determining whether said test compound inhibits the activity of said enzyme.

3. A method for detecting the activity of nucleic acid modification enzymes according to claim 1, wherein said nucleic acid modification enzyme is a ligase.

4. A method for detecting the activity of nucleic acid modification enzyme according to claim 1, wherein said nucleic acid modification enzyme is a helicase.

5. A method for detecting the activity of nucleic acid modification enzymes according to claim 1, wherein said template comprises a first oligo and a second oligo annealed thereto, wherein said second oligo and said labeled oligo form a double stranded nucleic acid substrate with said first oligo.

6. A method for detecting the activity of nucleic acid modification enzymes according to claim 5, further providing said break at a location between adjacent ends of said second oligo and said labeled oligo.

7. A method for detecting the activity of nucleic acid modification enzymes according to claim 5, wherein said double stranded nucleic acid substrate is a hairpin loop structure.

8. A method for detecting the activity of nucleic acid modification enzymes according to claim 7, further comprising mixing a test compound with said substrate and determining whether said test compound inhibits the activity of said nucleic acid modification enzyme.

9. A method for detecting the activity of nucleic acid modification enzymes according to claim 2, wherein said test compound has herbicidal activity, insecticidal activity or fungicidal activity.

10. A method for detecting the activity of nucleic acid modification enzymes according to claim 2, wherein said test compound has anti-tumor activity.

11. A method for detecting the activity of nucleic acid modification enzymes according to claim 2, wherein said test compound has antibiotic activity.

12. A method for detecting the activity of nucleic acid modification enzymes according to claim 2, wherein said test compound has antiviral activity.

13. A method for detecting the activity of nucleic acid modification enzymes according to claim 2, wherein said test compound has antileukemic activity.

14. A kit for detecting the activity of nucleic acid modification enzymes and inhibitors thereof comprising:

h) a substrate comprising a nucleic acid template and a fluorescently labeled oligo, wherein a portion of said template is complimentary to said labeled oligo and is annealed thereto, and a break is located between the adjacent ends of said template and said labeled oligo;

i) a support for retaining said substrate;

j) a nucleic acid modification enzyme for mixing with said substrate in said support to form a reaction mixture;

k) optionally, a stop reagent for adding to said reaction mixture; and l) means for measuring the fluorescence polarization signal of said reaction mixture.

* * * * *

SEQUENCE LISTING

<160> NUMBER OF SEQ ID NOS: 4

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence:
      Oliginucleotide

<400> SEQUENCE: 1
ttttgcctcg ctgccgtcgc cattttacgt cgtgacttct cactccagtc ctagtctaga    60

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:
      Oliginucleotide

<400> SEQUENCE: 2
taaaatggcg acggcagcga ggctttt                                        27

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence:
      Oliginucleotide

<400> SEQUENCE: 3
cacgacgtaa aatggcgacg gcagcgaggc tttt                                34

<210> SEQ ID NO 4
<211> LENGTH: 111
<212> TYPE: DNA
<213> ORGANISM: Artificial Sequence
<220> FEATURE:
<223> OTHER INFORMATION: Description of Artificial Sequence:
      Oliginucleotide

<400> SEQUENCE: 4
gactggagtg agaagtcacg acgtaaaatg gcgacggcag cgaggctaaa aaatagcctc    60
gctgccgtcg ccattttacg tcgtgacttc tcactccagt cctagtctag a             111